Sept. 16, 1952 E. S. BOERNER Plant Pat. 1,131
CHRYSANTHEMUM PLANT
Filed Sept. 28, 1951
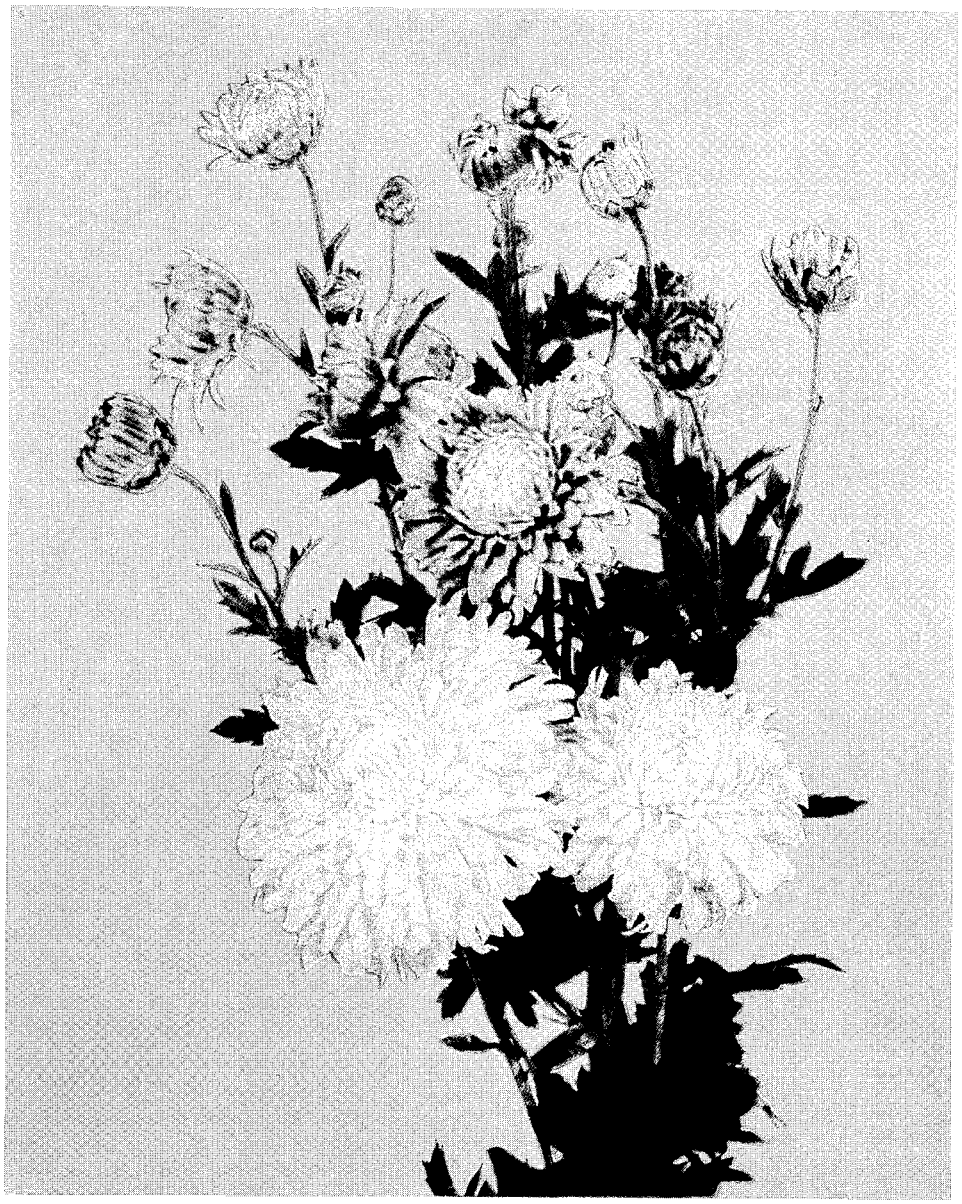
Inventor.
E. S. Boerner
By: Robbins Cobb
Attorneys Patented Sept. 16, 1952

Plant Pat. 1,131

UNITED STATES PATENT OFFICE 1,131

CHRYSANTHEMUM PLANT

Eugene S. Boerner, Newark, N. Y., assignor to Jackson & Perkins Company, Newark, N. Y., a corporation of New York Application September 28, 1951, Serial No. 248,793

1 Claim. (Cl. 47—60)

The present invention relates to a new and distinct variety of chrysanthemum plant, originated by me by crossing an unnamed and unpatented seedling of "Neta" × an unnamed and unpatented seedling of "Clara Curtis."

The primary objective of this cross was to produce a larger and hardier outdoor chrysanthemum of the "Clara Curtis" type. This result was fully achieved by using a very large-flowered seedling of "Neta" which is a semi-tender variety of orange color, and crossing this seedling by a seedling of "Clara Curtis."

This new variety is dominantly characterized by its vigorous and upright habits of growth, by its unusual hardiness and early-blooming habit, often commencing to bloom about August 15th in the climatic area of up-State New York, and continuing until heavy freezes in October and November, and by the Capucine Yellow color, overcast lightly with Capucine Orange, of its double, semi-decorative type flowers.

Asexual reproduction of this new variety by top cuttings and by underground runners at Newark, New York, shows that the foregoing characteristics come true to form and are established and transmitted through succeeding propagations.

The accompanying drawing shows specimens of the new variety, with the flowers and foliage in different stages of development.

The following is a detailed description of the new variety, as observed in the fields at Newark, New York, in the early morning hours in the latter part of the month of September, with color terminology in accordance with Ridgway's Color Standards and Nomenclature:

Parentage: A seedling of "Neta" × a seedling of "Clara Curtis."

Classification: Semi-decorative type.

Growth: Upright growth; attaining a height of 3½ to 4 feet.

Cold resistance: Hardy outdoors in northern New York and the flowers completely resistant to frost.

Blooming period: In Newark, New York climatic area, the average date of start of bloom is August 15th and continues until heavy freeze in October and November.

Bud:

*Color.*—When sepals first divide—Light Cadmium, Plate 4. When petals begin to unfurl—Bittersweet Orange, Plate 2. When half blown—inside of petals: Grenadine Red, Plate 2; reverse of petals: Scarlet, Plate 1.

*Peduncle.*—Color—Cress Green, Plate 31. Strength—stiff; erect.

Bloom:

*Size.*—3 to 3½ inches.

*Stems.*—Strong; normal.

*Form.*—Semi-decorative type.

*Petalage.*—Very double.

*Color.*—Center of flower—Capucine Yellow, Plate 3. Outer petals—Capucine Yellow, Plate 3. Base of petals — Orange-Buff, Plate 3. Inside of petals—Capucine Yellow, Plate 3, overcast lightly with Capucine Orange, Plate 3. Reverse of petals—Orange-Buff, Plate 3.

*Petals.*—Texture—medium. Form—straight, with slight wavy ends of petals.

*Fragrance*—Characteristic chrysanthemum.

Plant:

*Form.*—Compact; very good.

*Growth.*—Free.

Foliage:

*Size.*—Medium.

*Quantity.*—Normal.

*Color.*—Upper side—Cress Green, Plate 31; Reverse side—Light Elm Green, Plate 17.

*Texture.*—Leathery.

I claim:

A new and distinct variety of chrysanthemum plant, substantially as herein shown and described, characterized as to novelty by its vigorous and upright habits of growth, by its hardiness and its early-commencing and prolonged blooming habits, and by the distinctive color of its very double, semi-decorative type blooms.

EUGENE S. BOERNER.

No references cited.